US012578341B2

(12) United States Patent
Gut et al.

(10) Patent No.: US 12,578,341 B2
(45) Date of Patent: Mar. 17, 2026

(54) ITERATIVE FLUORESCENCE IMAGING

(71) Applicant: UNIVERSITÄT ZÜRICH, Zürich (CH)

(72) Inventors: Gabriele Gut, Zürich (CH); Lucas Pelkmans, Zurich (CH); Markus Herrmann, Boston, MA (US)

(73) Assignee: UNIVERSITÄT ZÜRICH, Zürich (CH)

( * ) Notice: Subject to any disclaimer, the term of this patent is extended or adjusted under 35 U.S.C. 154(b) by 1361 days.

(21) Appl. No.: 17/050,435

(22) PCT Filed: Apr. 24, 2019

(86) PCT No.: PCT/EP2019/060532
§ 371 (c)(1),
(2) Date: Oct. 24, 2020

(87) PCT Pub. No.: WO2019/207004
PCT Pub. Date: Oct. 31, 2019

(65) Prior Publication Data
US 2021/0140948 A1 May 13, 2021

(30) Foreign Application Priority Data

Apr. 24, 2018 (EP) .................................... 18169077

(51) Int. Cl.
*G01N 1/30* (2006.01)
*G01N 33/50* (2006.01)
*G01N 33/563* (2006.01)
*G01N 33/58* (2006.01)

(52) U.S. Cl.
CPC ............. *G01N 33/582* (2013.01); *G01N 1/30* (2013.01); *G01N 33/5091* (2013.01); *G01N 33/563* (2013.01); *Y10S 435/962* (2013.01)

(58) Field of Classification Search
CPC ............... G01N 33/563; G01N 33/582; G01N 33/5091; G01N 1/30
See application file for complete search history.

(56) References Cited

U.S. PATENT DOCUMENTS

2015/0167064 A1 * 6/2015 Gao ..................... G01N 33/588
506/9
2019/0346437 A1 * 11/2019 Ciftlik .................. C12Q 1/6832

FOREIGN PATENT DOCUMENTS

JP      2013046576      3/2013
WO      2017/137402      8/2017

OTHER PUBLICATIONS

Rogers et al. Thiol-reactive compounds prevent nonspecific antibody binding in immunohistochemistry. Laboratory Investigation 86: 526-533 (2006).*
Panagiotis Mitsopoulos et al, "Protective Effects of Liposomal N-Acetylcysteine against Paraquat-Induced Cytotoxicity and Gene Expression", Journal of Toxicology, vol. 2011, Jan. 1, 2011, pp. 1-14.
Arlin B Rogers et al, "Thiol-reactive compounds prevent nonspecific antibody binding in immunohistochemistry", Laboratory Investigation, vol. 86, No. 5, May 1, 2006 (May 1, 2006), p. 526-533.

* cited by examiner

*Primary Examiner* — Gailene Gabel
(74) *Attorney, Agent, or Firm* — JMB Davis Ben-David

(57) ABSTRACT

The invention relates to a method for multiplex staining of a biological sample involving the use of a buffer combination of blocking buffer, imaging buffer and elution buffer that allows for multiple staining rounds of biological samples. The blocking buffer comprises a compound that is capable of binding to hydrophobic binding sites non-specifically and a sulfhydryl-reactive compound. The imaging buffer is at neutral pH and comprises a radical scavenger, and the elution buffer is at pH lower than 4 and comprises a buffering component, a reducing agent and at least one compound disrupting hydrogen bonds. The invention further relates to buffers used in the practice of the method of the invention, and to a kit containing these buffers.

10 Claims, 8 Drawing Sheets

Fig. 3 (contd)
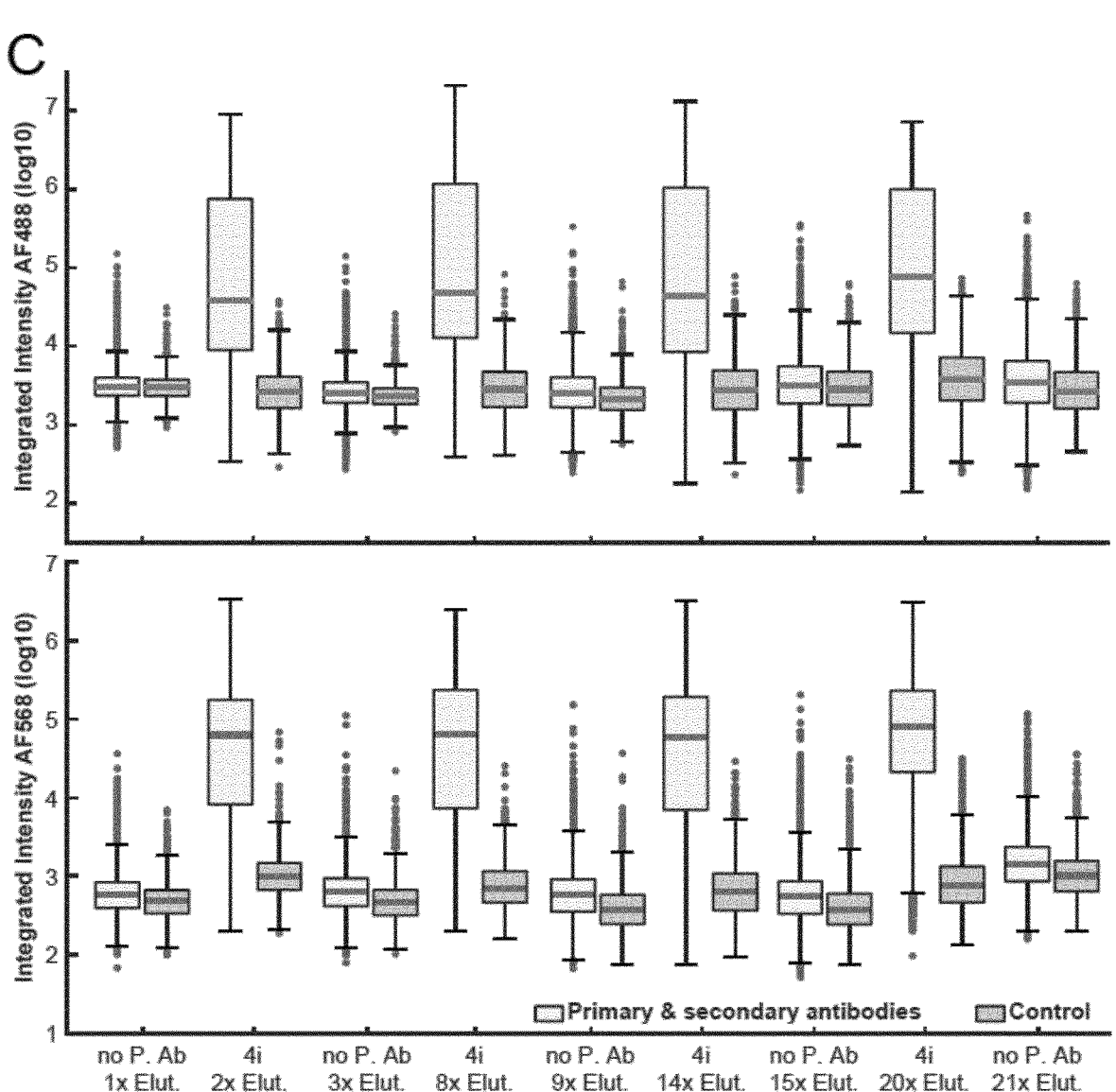

ITERATIVE FLUORESCENCE IMAGING

CROSS-REFERENCE TO RELATED APPLICATIONS

This is the U.S. National Stage of International Patent Application No. PCT/EP2019/060532 filed on Apr. 24, 2019, which claims the benefit of European Patent Application No. 18169077.7 filed on Apr. 24, 2018.

The present invention relates to a method that allows for multiplex antibody-staining of biological samples for imaging including buffers for blocking, imaging and elution.

BACKGROUND

Various methods have revolutionized our ability to obtain multiplexed measurements of the abundance of hundreds or thousands of different molecular species from single cells. These have brought the promise that through large-scale efforts, all functionally relevant cell types of a human body will, in an unbiased manner, emerge from such data. Since some of these methods can be applied in situ, the identified cell types can then be placed within the context of a cell population or tissue. However, it is well known that the abundance of a protein or protein state, or of an RNA transcript, is not directly informative about its involvement in cellular function. This depends on the specific intracellular location and interaction with other molecules and intracellular structures, which may only involve a small fraction of the total cellular pool. Moreover, the phenotype of an individual cell is determined by the functional state, abundance, morphology, and turnover of its intracellular organelles and cytoskeletal structures. Therefore, to obtain functionally relevant information, these unbiased large-scale methods need to extend the length scale of molecular multiplexing into the intracellular domain, and ultimately acquire temporal information. Recently, a tour-de-force study achieved high-resolution intracellular immunofluorescence imaging of 12,000 proteins, from which an average subcellular map of the human proteome was created. However, to understand how the subcellular distribution of the proteome is functionally linked to the phenotypic state of a cell and its microenvironment and how it responds to varying conditions, such maps must be directly measured in the same single cell and across many cells in situ. While various powerful methods exist that can achieve spatially resolved antibody multiplexing on tissues or single cells, none meet all requirements to simultaneously cover the tissue, single cell, and highly resolved intracellular length scale whilst preserving sample quality in a high-throughput manner for multiple conditions and be combined with large-scale image processing and multivariate statistical approaches to extract the rich amount of biological information present in such data.

The main issue with recording such multiplexed data is to allow for multiple antibody staining rounds without cross-linking the antibody to the sample.

The objective of this invention is to provide means and methods that allow for multiple antibody staining rounds without crosslinking the antibody to the sample.

This objective is attained by the subject matter of the independent claims of the present specification.

Terms and Definitions

The term 4i in the context of the present specification is an abbreviation for iterative indirect immunofluorescence imaging approach.

The term PBS in the context of the present specification relates to phosphate buffered saline with a concentration of 10 mmol/L $PO_4^{3-}$, 137 mmol/L NaCl, and 2.7 mmol/L KCl and a pH of 7.4.

The term BSA in the context of the present specification relates to bovine serum albumin.

The term FBS in the context of the present specification relates to fetal bovine serum.

The term SA in the context of the present specification relates to serum albumin of any species.

The term TCEP in the context of the present specification relates to tris(2-carboxyethyl)phosphine.

In the context of the present specification, the term biological sample prepared for imaging refers to any biological material that is fixed on a device usable for imaging, particularly but not limited to fluorescence microscopy. The biological sample prepared for imaging may be selected from but is not limited to paraformaldehyde-fixed single cells or cell conglomerats (e.g. organoids, spheroids) or tissue or sections of biological material of different preparations such as Formalin-Fixed Paraffin-Embedded or Fresh Frozen directly on or supported by a 3D-organic or inorganic matrix on a glass slide or multiwell plates (glass/plastic) or any other type of specimen holder suitable for microscopy.

In the context of the present specification, the term antibody refers to whole antibodies including but not limited to immunoglobulin type G (IgG), type A (IgA), type D (IgD), type E (IgE) or type M (IgM), any antigen binding fragment or single chains thereof and related or derived constructs. A whole antibody is a glycoprotein comprising at least two heavy (H) chains and two light (L) chains interconnected by disulfide bonds. Each heavy chain is comprised of a heavy chain variable region (VH) and a heavy chain constant region (CH). The heavy chain constant region is comprised of three domains, $C_H1$, $C_H2$ and $C_H3$. Each light chain is comprised of a light chain variable region (abbreviated herein as VL) and a light chain constant region ($C_L$). The light chain constant region is comprised of one domain, $C_L$. The variable regions of the heavy and light chains contain a binding domain that interacts with an antigen. Similarly, the term encompasses a so-called nanobody or single domain antibody, an antibody fragment consisting of a single monomeric variable antibody domain.

In the context of the present specification, the term labelled antibody is used for an antibody being covalently bound to a detectable label. Such detectable labels include for example, without limitation, octadecyl rhodamine B, 7-nitro-2-1,3-benzoxadiazol-4-yl, 4-acetamido-4'-isothiocyanatostilbene-2,2' disulfonic acid, acridine and derivatives, 5-(2'-aminoethyl)amino-naphthalene-1-sulfonic acid (EDANS), 4-amino-N-(3-[vinylsulfonyl]phenyl)naphthalimide-3,6-disulfonate dilithium salt, N-(4-anilino-1-naphthyl)maleimide, anthranilamide, BODIPY, Brilliant Yellow, coumarin and derivatives, cyanine dyes, cyanosine, 4',6-diaminidino-2-phenylindole (DAPI), bromopyrogallol red, 7-diethylamino-3-(4'-isothiocyanatophenyl)-4-methylcoumarin, diethylenetriamine pentaacetate, 4,4'-diisothiocyanatodihydro-stilbene-2,2'-disulfonic acid, 4,4'-diisothiocyanatostilbene-2,2'-disulfonic acid, dansylchloride, 4-dimethylaminophenylazophenyl-4'-isothiocyanate (DABITC), eosin and derivatives, erythrosin and derivatives, ethidium, fluorescein, 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein isothiocyanate, X-rhodamine-5-(and 6)-isothiocyanate (QFITC or XRITC), fluorescamine, IR-144 (2-[2-[3[[1,3-dihydro-1,1-dimethyl-3-(3-sulfopropyl)-2H-benz[e]indol2- ylidene]-ethylidene]-2-[4-(ethoxycarbonyl)-1-piperazinyl]-1-cyclopenten-1-yl]ethenyl]-1,1-dimethyl-3-(3-sulforpropyl)-1H-benz[e]indolium hydroxide, inner salt, compound with n,n-diethylethanamine(1:1), CAS No.: 54849-69-3), 5-chloro-2-[2-[3-[(5-chloro-3-ethyl-2(3H)-benzothiazol-ylidene)ethylidene]-2-(diphenylamino)-1-cyclopenten-1-yl]ethenyl]-3-ethyl benzothiazolium perchlorate (IR140), malachite green isothiocyanate, 4-methylumbelliferone, ortho cresolphthalein, nitrotyrosine, pararosaniline, phenol red, B-phycoerythrin, o-phthaldialdehyde, pyrene, pyrene butyrate, succinimidyl 1-pyrene, butyrate quantum dots, Reactive Red 4 (Cibacron Brilliant Red 3B-A), rhodamine and derivatives, 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'tetramethyl-6-carboxyrhodamine (TAM RA) tetramethyl rhodamine, tetramethyl rhodamine isothiocyanate (TRITC), riboflavin, rosolic acid, terbium chelate derivatives, Cyanine-3 (Cy3), Cyanine-5 (Cy5), Cyanine-5.5 (Cy5.5), Cyanine-7 (Cy7), IRD 700, IRD 800, Alexa 647, La Jolta Blue, phthalo cyanine, and naphthalo cyanine.

In the context of the present specification, the term radical scavenger is used for a compound that quickly reacts with and thereby removes free radicals.

In the context of the present specification, the term washing solution is used for a solution that is capable of washing off the remaining components of any of the other buffer or staining solutions employed herein that are not specifically bound to the sample. The washing solution does not remove specifically bound ligands (antibodies etc.) from the sample.

In the context of the present specification, the term multiplex staining is used for a method whereby a biological sample is stained with more than one species of (primarily or secondarily) labelled antibody, in other words more than one antigen is detected.

DETAILED DESCRIPTION OF THE INVENTION

A first aspect of the invention relates to a method for multiplex staining of a biological sample with a labelled antibody or an antibody-like ligand capable of specifically binding to a particular antigen.

The method comprises the following steps:

(a) In a blocking step, a biological sample prepared for imaging is contacted with a blocking solution that is used to reduce non-specific binding of an antibody used in a later staining step, where this unspecific binding would cause high background staining. The blocking solution comprises a blocking compound that is capable of binding to hydrophobic binding sites non-specifically, and a sulfhydryl-reactive compound that prevents the formation of disulfide bridges, which might cause covalent binding of the antibody to the sample. Subsequently, the blocking solution is removed.

(b) In a first washing step, said biological sample is contacted with a washing solution and subsequently the washing solution is removed. Optionally, the first washing step may be repeated one to ten times, particularly 3 to 6 times.

(c) In a first staining step, said biological sample is contacted with a first antibody specific for a first antigen. In certain embodiments, said first antibody bears a detectable label, particularly a fluorescent label. Then, steps d and e are obsolete. If said first antibody does not bear a detectable label, a second staining step is required.

(d) In a second washing step, said biological sample is contacted with a washing solution and subsequently the washing solution is removed. Optionally, the first washing step may be repeated one to ten times, particularly 3 to 6 times.

(e) In a second staining step, said biological sample is contacted with a second antibody bearing a detectable label, particularly a fluorescent label, and said second antibody is specific for the first antibody.

(f) In a third washing step, said biological sample is contacted with a washing solution and subsequently the washing solution is removed. Optionally, the first washing step may be repeated one to ten times, particularly 3 to 6 times.

(g) In an imaging step, said biological sample is contacted with an imaging solution that has a neutral pH and contains a radical scavenger. Subsequently, a fluorescence image of the sample is recorded and afterwards the imaging solution is removed.

(h) In a fourth washing step, said biological sample is contacted with a washing solution and subsequently the washing solution is removed. Optionally, the first washing step may be repeated one to ten times, particularly 3 to 6 times.

(i) In an elution step, said biological sample is contacted with an elution solution that is selected to elute the bound antibody or antibodies from the sample. The elution solution has a pH lower than (<) 4, particularly pH<3, more particularly ≤2, 7 and comprises a buffering component, a reducing agent and at least one compound disrupting hydrogen bonds. Subsequently, the elution solution is removed.

In certain embodiments, the steps a to i are repeated 1, 2, 3, 4, 5 or more (≥5), ≥10, ≥15, ≥20, ≥25, ≥30, ≥35, or even ≥40 times, employing a different first antibody in each repeat.

Eluting ability of antibodies using this method was explored by overlaying images obtained with the same antibody in a 1st, 11th, and 21st round of staining. This resulted in an almost perfect overlay for various types of intracellular structures, and in very high single-cell and single-pixel intensity correlations between all rounds.

With conventional buffers, the elution efficiency was strongly compromised in the region that was exposed to light, presumably due to photo-crosslinking of the antibody to the sample.

In certain embodiments, directly before the imaging step, a nucleus-labelling step is performed, contacting said biological sample with a DNA-binding fluorescent compound, followed by a washing step, contacting said biological sample with the washing solution and subsequently removing the washing solution, optionally repeating the first washing step one, two, three, four, five or six times.

In certain embodiments, the detectable label of the labelled antibody is a fluorophore.

In certain embodiments, imaging of the biological sample is performed as fluorescence microscopy, particularly confocal fluorescence microscopy.

In certain embodiments, the washing solution is composed of $H_2O$ or PBS, particularly of PBS or $H_2O$ only.

In certain embodiments, the blocking compound in the blocking solution is a blocking polypeptide not being recognized by any of the antibodies employed in the first or second staining step.

In certain embodiments, the blocking polypeptide is selected from BSA, FBS, SA, human serum, gelatin, skim milk powder or a polypeptide fraction of highly purified dermal collagen of porcine origin (Prionex® Reagent).

In certain embodiments, the sulfhydryl-reactive compound is selected from maleimide, haloacetyl, or pyridyl disulfide.

In certain embodiments, the blocking solution comprises 0.5 to 2%, particularly ca. 1% of a compound selected from BSA, FBS, SA, normal serum, gelatin, skim milk powder or Prionex® Reagent and/or 1 mmol/L to 1 mol/L, particularly 10 mmol/L to 500 mol/L of maleimide, haloacetyl, or pyridyl disulphide.

In certain embodiments, the blocking solution comprises 1% BSA and 150 mM maleimide in PBS.

In certain embodiments, the compound in the elution solution disrupting hydrogen bonds is a chaotropic salt.

In certain embodiments, the buffering component of the elution solution is selected from L-glycine, phosphate/citrate or potassium hydrogen phthalate.

In certain embodiments, the reducing agent is selected from TCEP, dithiothreitol, or 2-mercaptoethanol.

In certain embodiments, the chaotropic salt is selected from one or more of guanidinium chloride, urea, sodium dodecyl sulfate or magnesium chloride.

In certain embodiments, the elution solution comprises 0.5 M L-glycine and 1 mmol/L to 1 mol/L of a compound selected from TCEP, dithiothreitol, or 2-mercaptoethanol and/or 1 mmol/L to 10 mol/L of one or more of guanidinium chloride, urea, sodium dodecyl sulfate or magnesium chloride and/or a pH of 2.2-2.6.

In certain embodiments, the elution solution comprises 0.5 M L-glycine, 70 mM TCEP, 3 M guanidinium chloride and 3 M urea in $H_2O$ at pH 2.5.

In certain embodiments, the radical scavenger is selected from N-acetylcysteine, N-acetylcysteine amide, cysteine, L-ascorbic acid, resveratrol, β-carotene, seleno-L-methionine, chlorogenic acid and/or caffeic acid.

In certain embodiments, the imaging solution comprises 1 mmol/L to 1 mol/L of a compound selected from N-acetylcysteine, N-acetylcysteine amide, cysteine, L-ascorbic acid, resveratrol, β-carotene, seleno-L-methionine, chlorogenic acid or caffeic acid, and/or a pH of 7.2-7.6.

In certain embodiments, the imaging solution comprises 700 mM N-acetylcysteine in $H_2O$, at pH 7.4.

In certain embodiments, the first antibody is incubated for 10 minutes to 16 hours.

In certain embodiments, the second antibody is incubated for 10 min to two hours.

In certain embodiments, the blocking solution is incubated for 5 min to one hour.

In certain embodiments, the elution solution is incubated for 1 minute to 30 minutes.

In certain embodiments, all mentioned steps are performed at room temperature.

A second aspect of the invention relates to a blocking buffer comprising (a) a blocking compound that is capable of binding to hydrophobic binding sites non-specifically, particularly a blocking polypeptide, more particularly a blocking polypeptide selected from BSA, FBS, SA, normal serum, gelatin, skim milk powder or Prionex® Reagent, even more particularly 0.5 to 2% of a compound selected from BSA, FBS, SA, normal serum, gelatin, skim milk powder or Prionex® Reagent, most particularly 1% BSA and (b) a sulfhydryl-reactive compound, particularly a compound that is selected from maleimide, haloacetyl, or pyridyl disulphide, more particularly 1 mmol/L to 1 mol/L, particularly 10 mmol/L to 500 mol/L, of a compound selected from maleimide, haloacetyl, or pyridyl disulphide, most particularly 150 mM maleimide and (c) a buffering component, particularly PBS.

A third aspect of the invention relates to an imaging buffer comprising (a) a radical scavenger, particularly a compound that is selected from N-acetylcysteine, N-acetylcysteine amide, cysteine, L-ascorbic acid, resveratrol, β-carotene, seleno-L-methionine, chlorogenic acid and/or caffeic acid, more particularly 1 mmol/L to 1 mol/L of a compound selected from N-acetylcysteine, N-acetylcysteine amide, cysteine, L-ascorbic acid, resveratrol, β-carotene, seleno-L-methionine, chlorogenic acid or caffeic acid, most particularly 700 mM N-acetylcysteine and (b) a pH of 7.2-7.6, particularly a pH of 7.4.

A fourth aspect of the invention relates to an elution buffer comprising (a) a reducing agent, particularly a compound that is selected from TCEP, dithiothreitol, or 2-mercaptoethanol, more particularly 1 mmol/L to 1 mol/L of a compound that is selected from TCEP, dithiothreitol, or 2-mercaptoethanol, most particularly 70 mM TCEP and (b) at least one compound disrupting hydrogen bonds, particularly a chaotropic salt, more particularly a compound that is selected from guanidinium chloride, urea, sodium dodecyl sulfate or magnesium chloride, more particularly 1 mmol/L to 10 mol/L of one or more of guanidinium chloride, urea, sodium dodecyl sulfate or magnesium chloride, most particularly 3 M guanidinium chloride and 3 M urea and (c) a buffering component, particularly L-glycine, more particularly 0.5 M L-glycine and (d) a pH lower than (<) 4, particularly pH <3, more particularly ≤2,7.

A fifth aspect of the invention relates to a kit of parts (set) comprising a blocking buffer according to the second aspect and an imaging buffer according to the third aspect and an elution buffer according to the fourth aspect.

In certain embodiments, the kit comprises additionally instructions to proceed according to the method of the first aspect.

Wherever alternatives for single separable features such as, for example, a radical scavenger or blocking polypeptide are laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

BRIEF DESCRIPTION OF THE FIGURES

FIG. 1 4i achieves at least 40-plexed spatially resolved molecular readouts from the same cell, whilst remaining highly reproducible at the single-cell and pixel level. (A) Image acquisition of fluorescence signals causes photo crosslinking of antibodies to the sample. Immunofluorescence (IF) against TUBA1A was performed. The sample was imaged without Imaging Buffer (1, orange box, gray represents non-imaged well areas). Antibodies were then eluted from the sample. The sample was then incubated with secondary antibodies and imaged a second time, in a tailed fashion (green boxes) to record fluorescence both in areas which have and have not been exposed to laser light, respectively (2). The former clearly show higher signal, exemplifying the effect of light in crosslinking primary antibodies to the sample. Images from first and second imaging are rescaled independently. (B) 4i elutes primary and secondary antibodies from the sample after image acquisition, whilst retaining epitope integrity. Boxplots of integrated cell intensity for multiple primary antibodies detected by secondary antibodies labelled with Alexa Fluor 588 (left) and Alexa Fluor 568 (right). Background intensity was quantified by incubating cells solely with secondary antibodies (1st boxplot from the left). Cell intensities were measured after 2 and 20 elutions (2nd and 4th boxplot from the left), showing similar dynamic ranges. Cell intensities were reduced to background after elution of primary and secondary antibody complex and restaining with secondary antibody only (3rd and 5th boxplot from the left) (FIG. 3B). Boxplot is constructed as follows: central mark indicates population median, box indicates population range between 25th and 75th percentile, whiskers cover of 99.3% of population range, outliers are marked as dots. (C) Composite images of the same cells stained with either CTNNB1 or TUBA1A from cycle 1, 11 and 21 or cycle 2, 10 and 20, respectively. Images from cycle 1 and 2 are colored in cyan, from cycle 11 and 10 in magenta, from cycle 21 and 20 in yellow. Areas of high colocalization between the three cycles appear white. Images of different 4i cycles were rescaled differently prior to creation of the composite image. (D) 4i retains high correlations of integrated single cell intensities over 21 cycles of iterative IF. Boxplot represent single-cell correlations of integrated cell intensity measured for either CTNNB1 or TUBA1A over all cycles for all cycles with each other. Boxplot is constructed as follows: central mark indicates population median, box indicates population range between 25th and 75th percentile, whiskers cover of 99.3% of population range, outliers are marked as dots. Number of cells 16,000. (E) 4i retains high pixel intensity correlations over 21 cycles of iterative IF. Boxplots represent pixel intensity correlations measured between cells over 21 4i cycles for CTNNB1 with itself (cyan), TUBA1A with itself (green), and CTNNB1 with TUBA1A (purple) in images smoothed by a mean filter of increasing size (none, 2×2, 3×3, 5×5, 7×7, and 10×10 pixel) (FIG. 3D,E). Boxplot is constructed as follows: central mark indicates population median, box indicates population range between 25th and 75th percentile, whiskers cover of 99.3% of population range, outliers are marked as dots. Number of cells 16,000.

FIG. 3 4i protocol optimization (A) Imaging Buffer prevents cross linking of antibodies to sample during image acquisition. Micrographs of cells stained for TUBA1A using primary and secondary antibodies (first two panels for the left) and of cells incubated with secondary antibodies only (third panel from the left, Ctrl). 4i was performed in cells against TUBA1A (first two panels from the left, primary and secondary antibody), as well as only with secondary antibodies (Ctrl, third panel from the left). Antibodies were eluted from sample (first micrograph of each panel), sample cells were then incubated with secondary antibody only to probe for complete elution of primary antibodies (second micrograph of each panel), and restained for TUBA1A (third micrograph of each panel). Micrographs of individual panels were rescaled the same. Micrographs in first panel was rescaled differently to second and third panel. (B) Maleimide treatment in sample blocking aids antibody elution while retaining structural integrity of the sample. Scatter plots in the upper row visualize on the X axis mean values of correlations quantified in single cells for pixel intensities measured between signal acquired after immunofluorescence (Stain1) and restaining with only the secondary antibody after sample elution (SecAbRestain) and on the Y axis mean values of correlations quantified in single cells for pixel intensities measured between signal acquired after immunofluorescence (Stain1) and the second round of immunofluorescence after antibody elution (Stain 2) using secondary antibodies labeled with AlexaFluor 488 (upper left) or AlexaFluor 568 (upper right). Highest correlations values between Stain 1 and 2, as well as lowest correlation values between SecAbRestain and Stain 1 are achieved by adding Maleimide to the Blocking Buffer. Same analysis was performed quantifying correlations of single cell intensities, leading to the same result (lower row) (C) Boxplots of integrated cell intensity measured for antibodies raised in mouse (secondary antibody goat anti mouse Alexa Fluor 488) used for the experiment over 20 cycles of 4i. Gray boxplots represent cell intensities measured in cells, which were incubated with both primary and secondary antibodies. Blue boxplots represent cell intensities measured in cells, which were incubated solely with secondary antibodies. These serve as a control to quantify buildup of background signal due to unspecific binding of secondary antibody, incomplete elution of primary and secondary antibodies from the sample and epitope stability. Similarity throughout the experiment between the white boxplots representing immunofluorescence show stable dynamic range for 20 cycles of 4i, as well as successful elution of antibodies from the sample over 20 cycles of 4i, exemplified by similarity of the white and the blue boxplots at all steps of restaining the sample only with secondary antibodies (no P. Ab). Finally, no buildup of background signal was detected, highlighted by similarity of the blue boxplots at all stages of the experiment. Same experiment and results as described in upper row, but with primary antibodies raised in rabbit (and secondary antibodies goat anti rabbit Alexa Fluor 568). Boxplot is constructed as follows: central mark indicates population median, box indicates population range between 25th and 75th percentile, whiskers cover of 99.3% of population range, outliers are marked as dots. (D) Bar graphs represent correlations (Pearson in blue and Spearman in green) integrated cell intensity of PCNA, FBL, CTNNB1 and TUBA1A for cycles 1 to 21 compared to cycle of the first staining (cycle 1 for PCNA and CTNNB1, cycle 2 for FBL and TUBA1A). (E) 4i retains high pixel intensity correlations over 21 cycles of iterative IF. Boxplots represent pixel intensity correlations measured between cells over 21 4i cycles for PCNA with itself (cyan), FBL with itself (green), and PCNA with FBL (purple) in images smoothed by a mean filter of increasing size (none, 2×2, 3×3, 5×5, 7×7, and 10×10 pixel). Boxplot is constructed as follows: central mark indicates population median, box indicates population range between 25th and 75th percentile, whiskers cover of 99.3% of population range, outliers are marked as dots.

EXAMPLES

Materials and Methods

Figure 1:
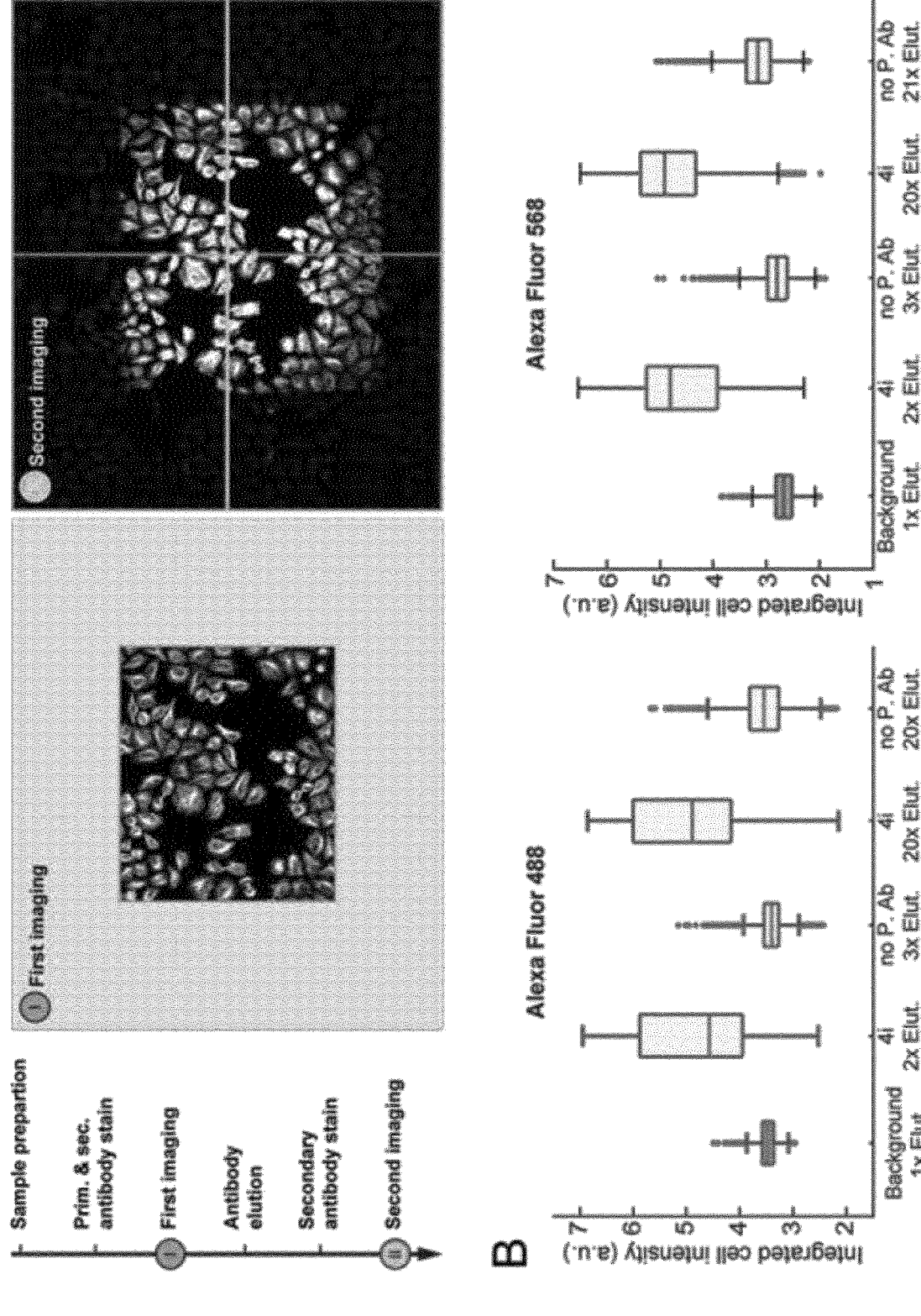
Figure 1:
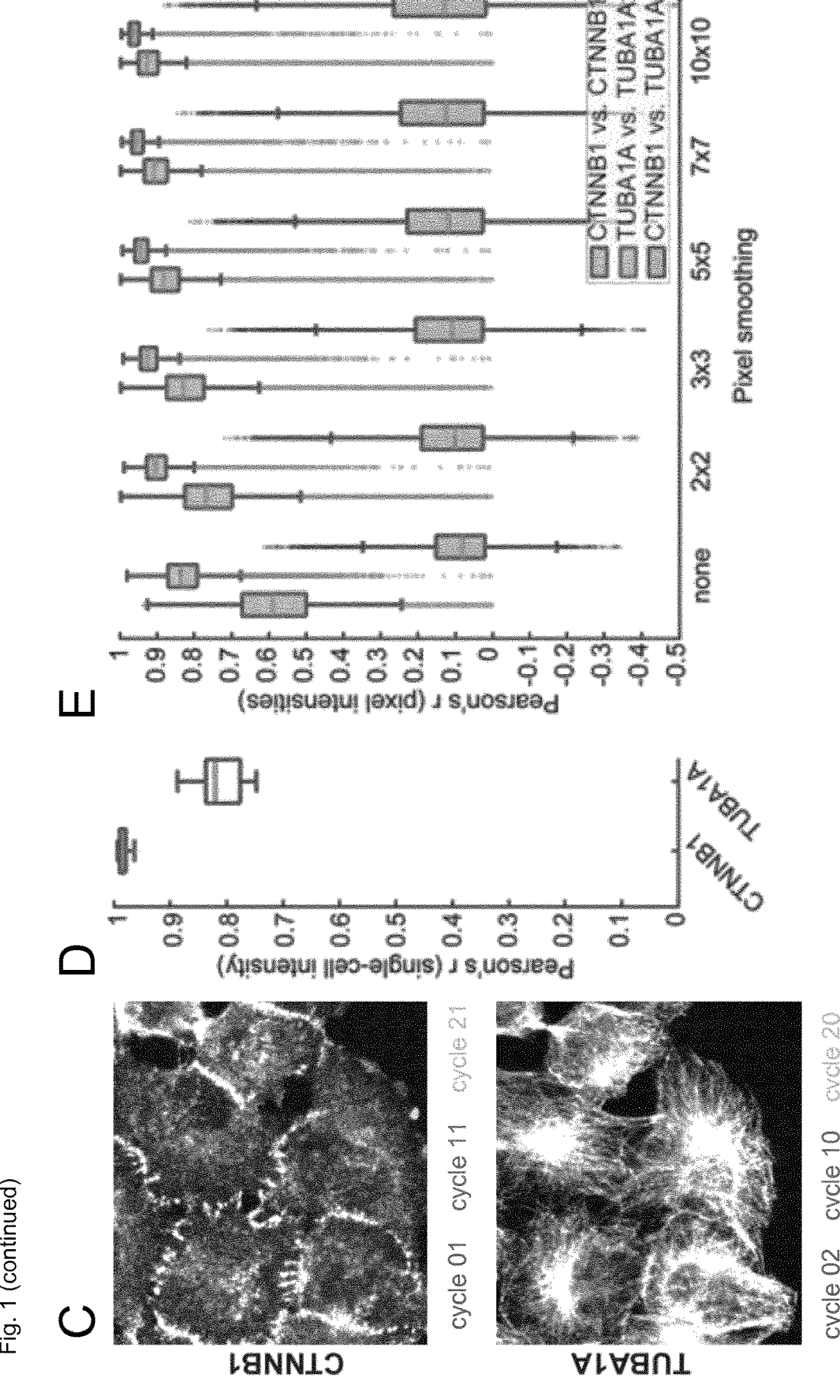

Cell Culture
Cell Line
HeLa Kyoto (Human cervical epithelial cell line, Prof. J. Ellenberg laboratory, EMBL, Germany). Cells were tested for identity by karyotyping and tested for absence of myco-plasm before use.
Complete Medium(CM)
CM consists of 10% Fetal Bovine Serum (FBS), and 5% Glutamine in DMEM. DMEM (Lifetechnologies), Fetal Bovine Serum (Sigma Aldrich), Glutamine (Lifetechnolo-gies).
Pharmacological Perturbations
Epidermal Growth Factor (EGF) (Milipore), Nocodazole (Sigma Aldrich), Latrunculin A (Sigma Aldrich), Bafilomy-cin Al (Sigma Aldrich), Brefeldin A (Sigma Aldrich), Wort-mannin (Sigma Aldrich), Rapamycin (Sigma Aldrich).
Iterative Indirect Immunofluorescence Imaging (4i)
4i Blocking Solution (sBS)
sBS consists of 1% Bovine Serum Albumine (BSA), and 150 mM Maleimide in phosphate buffered saline (PBS).

Maleimide is added to aqueous solution just before Block-ing step in 4i protocol. BSA (Sigma Aldrich), Maleimide (Sigma Aldrich)
Conventional Blocking Solution (cBS)
cBS consists of 1% Bovine Serum Albumine (BSA) in phosphate buffered saline (PBS). BSA (Sigma Aldrich)
Imaging Buffer (IB)
IB consists of 700 mM N-Acetyl-Cysteine (NAC) in $dH_2O$.
Adjust to pH7.4.
NAC (Sigma Aldrich)
Elution Buffer (EB)
EB consists of 0.5M L-Glycine, 3M Urea, 3M Guanidi-num chloride (GC), and 70 mM TCEP-HCl (TCEP) in $ddH_2O$.
Adjust to pH2.5.
L-Glycine (Sigma-Aldrich), Urea (Sigma-Aldrich), GC (Sigma-Aldrich), TCEP (Sigma-Aldrich).
Primary Antibodies
Antibodies were selected based on the following criteria: 1. Successful use of antibody in immunofluorescence has been published in the past in scientific literature. 2. Antibody is raised against epitopes on bona fide markers of organelles. 3. To ensure same number of antibodies raised in both mouse and rabbit.

Antibodies raised in mouse

| Cycle | Name | Conc. (1/x) | Clonality | Manufacturer | Product ID |
|---|---|---|---|---|---|
| 1 | LAMP1 | 250 | monoclonal | BD Biosciences | 555798 |
| 2 | RAB11 | 200 | monoclonal | Cell Signaling | 5589 |
| 3 | TSG101 | 100 | monoclonal | Santa Cruz Biotechnology | sc-7964 |
| 4 | EGFR | 150 | monoclonal | Santa Cruz Biotechnology | sc-373746 |
| 5 | HSP60 | 1000 | monoclonal | Abcam | ab13532 |
| 6 | ABCD3 | 300 | monoclonal | Sigma Life Science | AmAb90995 |
| 7 | CCNE1 | 150 | monoclonal | Abcam | ab3927 |
| 8 | ISG15 | 200 | monoclonal | Santa Cruz Biotechnology | sc-166755 |
| 9 | c-MYC | 150 | monoclonal | Santa Cruz Biotechnology | sc-40 |
| 10 | EEA1 | 150 | monoclonal | BD Biosciences | 610457 |
| 11 | TFRC | 200 | monoclonal | ThermoFisher Scientific | 13-6800 |
| 12 | VIME | 500 | monoclonal | Abcam | ab8978 |
| 13 | p-FAK | 200 | Monoclonal | BD Biosciences | 611722 |
| 14 | GM130 | 300 | monoclonal | BD Biosciences | 610822 |
| 15 | CTNNB1 | 300 | monoclonal | Cell Signaling Technology | 2677 |
| 16 | Actin | 200 | Monoclonal | Abcam | ab3280 |
| 17 | TUBA1A | 500 | monoclonal | Abcam | ab7291 |
| 18 | NUPS | 1000 | monoclonal | Abcam | ab24609 |
| 19 | Yap/Taz | 200 | monoclonal | Santa Cruz Biotechnology | 101199 |
| 20 | Climp63 | 1000 | monoclonal | Enzo | ALX-804-604 |
| 21 | VINC | 500 | monoclonal | Sigma-Aldrich | V9131 |

Antibodies raised in rabbit

| Cycle | Name | Conc. (1/x) | Clonality | Manufacturer | Product ID |
|---|---|---|---|---|---|
| 1 | LC3B | 250 | polyclonal | MBL | PM036 |
| 2 | p-ERK | 300 | polyclonal | Cell Signaling Technology | 9101 |
| 3 | p-AKT | 200 | monoclonal | Cell Signaling Technology | 13038 |
| 4 | p-AMPK | 200 | monoclonal | Cell Signaling Technology | 2535 |
| 5 | p-GSK3B | 200 | monoclonal | Cell Signaling Technology | 9323 |
| 6 | PKM2 | 200 | polyclonal | Novus Biologicals | NBP1-48308 |
| 7 | EIF1a | 200 | polyclonal | Cell Signaling Technology | 9721 |
| 8 | GSK3A/B | 200 | monoclonal | Cell Signaling Technology | 5676 |
| 9 | CCNB1 | 200 | monoclonal | Cell Signaling Technology | 12231 |
| 10 | p-RPS6 | 200 | polyclonal | Cell Signaling Technology | 2211 |

-continued

| Antibodies raised in rabbit | | | | | |
|---|---|---|---|---|---|
| Cycle | Name | Conc. (1/x) | Clonality | Manufacturer | Product ID |
| 11 | CAV1 | 200 | polyclonal | Santa Cruz Biotechnology | sc-894 |
| 12 | p-4EBP1 | 150 | monoclonal | Cell Signaling Technology | 2855 |
| 13 | SARA | 150 | polyclonal | Santa Cruz Biotechnology | sc-9135 |
| 14 | p-MEK | 150 | polyclonal | Cell Signaling Technology | 9121 |
| 15 | CRT | 1000 | polyclonal | Abcam | 2907 |
| 16 | PCNA | 300 | monoclonal | Cell Signaling Technology | 13110 |
| 17 | p-EGFR | 250 | polyclonal | ThermoFischer Scientific | 36-9700 |
| 18 | PCNT | 1000 | polyclonal | Abcam | ab4448 |
| 19 | FBL | 750 | polyclonal | Abcam | ab5821 |
| 20 | TGN46 | 300 | polyclonal | Sigma-Aldrich | T7576 |
| 21 | p-ERK | 300 | polyclonal | Cell Signaling Technology | 9101 |

Whilst testing antibodies for this publication, two (antibody against epitope on TOM20 (Abcam ab56783) and CAT (Abcam ab110292)) out of more than 50 antibodies were identified to not work together with the 4i protocol.

Secondary Antibodies

Anti-mouse AlexaFluor-488 was diluted 1:600 and anti-rabbit AlexaFluor-568 was diluted 1:300 in cBS respectively.

Anti-mouse AlexaFluor-488 (Lifetechnologies), anti-rabbit AlexaFluor-568 (Lifetechnologies)

DNA Stain Solution (DSS)

4',6-diamidino-2-phenylindole (DAPI) diluted 1:250 to 1:50 in PBS.

DAPI concentration was increased with increasing numbers of elutions to compensate for signal lost due to depurination of DNA, and the resulting reduced binding affinity of DAPI. DAPI (Lifetechnologies)

Computational Infrastructure

Image analysis steps were performed on the high-performance cluster computer Brutus at ETH Zürich. Extraction of multiplexed pixel profiles, as well as their clustering using self-organizing algorithms were performed on Science Cloud UZH. All other described computational methods were executed on a desktop computer.

Supplementary Methods

Cell Culture

Cells were cultured in Complete Medium at 37° C., 95% Humidity and 5% $CO_2$. 750 cells per well were seeded in a 384-well plate (Greiner) and were grown for 3 days in the above mentioned conditions.

Pharmacological and Metabolic Perturbations

All compounds were diluted in to their respective final concentration using Complete Medium, except for EGF, which was diluted in DMEM only.

Pharmacological Perturbations:

Cells were incubated for 3 h with compounds.

Metabolic Perturbations

| | Overnight growth factor starvation in Optimem (GFS) | GFS followed by 3 h EGF stimulation (S + EGF) | 3 h EGF stimulation (EGF) |
|---|---|---|---|
| EGF concentration | 0 ng/ml | 100 ng/ml | 100 ng/ml |

Microscopy

An automated spinning disk microscope from Yokogawa (CellVoyager 7000) with an enhanced CSU-W1 spinning disk (Microlens-enhanced dual Nipkow disk confocal scanner, wide view type) was used in combination with a 40× Olympus objective of 0.95 NA, and Neo sCMOS cameras (Andor, 2,560×2,160 pixels) to acquire microscopy images. 18 z-planes with a 500 nm z-spacing were acquired per site and a maximum intensity projection was computed and used for subsequent image analysis. UV (406 nm), green (488 nm) and red (568 nm) signals were acquired sequentially.

Iterative Indirect Immunofluorescence Imaging (4i)

Sample Preparation

If not stated differently, all steps were performed at room temperature. Cells were fixed in 4% Paraformaldehyde (Electron Microscopy Sciences) for 30 min. Cells were then permeabilized with 0.5% Triton X-100 for 15 min. Cells were washed 6 times with PBS both before and after permeabilization. Fixation and permeabilization were performed at room temperature.

Immunofluorescence

Each of the subsequent steps was performed in sequence of their mentioning and in every cycle of 4i. If not stated differently, all steps were performed at room temperature.

1. Antibody Elution

Sample was washed 6 times with $ddH_2O$. Residual $ddH_2O$ was aspirated to minimal volume.

Subsequent actions are repeated 3 times: EB was added to sample and shaken at 100 rpm for 10 min. Then EB was aspirated to minimal volume possible.

| | Nocodazole (NOC) | Latranculin A (LATA) | Bafilomycin A1 (BAF) | Brefeldin A (BRF) | Wortmannin (WRT) | Rapamycin (RPA) |
|---|---|---|---|---|---|---|
| Concentration | 500 ng/ml | 0.2 mM | 100 mM | 2.5 mg/ml | 1 mM | 0.5 mM |

2. Blocking sBS was added to sample shaken at 100 revolutions per minutes (rpm) for 1 h.

After 1 h sample was washed 6 times with PBS.

3. Indirect immunofluorescence, primary antibody stain

Primary antibody solution was added to sample and shaken at 100 rpm for 2 h.

After 2 h sample was washed 6 times with PBS.

4. Indirect immunofluorescence, secondary antibody stain

Secondary antibody solution was added to sample and shaken at 100 rpm for 2 h.

After 2 h sample was washed 6 times with PBS.

5. Nuclear staining

DSS was added to sample and shaken at 100 rpm for 10 min.

After 10 min sample was washed 6 times with ddH$_2$O. Residual ddH$_2$O was aspirated to minimal volume.

6. Imaging

IB was added to sample and sample was imaged.

7. Perform step 1 to 6 until required plexity is achieved.

All liquid dispensing and washing steps of the 4i protocol were performed using a Washer Dispenser EL406 (BioTek). Primary and secondary antibodies were dispensed using a Bravo liquid handling platform from Agilent Technologies. Antibody Elutability and Dynamic Range Preservation Over 20 4i Cycles To test sample stability, elution of primary and secondary antibody from the sample, and potential back ground signal increase from non-specific binding of secondary antibody over 20 4i cycles the following experiment was performed. (1) The sample was first treated with EB (1× Elut.), (2) then stained only with secondary antibody to record the fluorescence background level (SecAb only). (3) Subsequently the sample was treated with EB (2× Elut.) and then (4) incubated with both primary and secondary antibodies in test wells and only with secondary antibodies in control wells (IF). (5) Primary and secondary antibodies were eluted from the sample (3× Elut.) and (6) the sample was incubated with secondary antibodies only (SecAb only) in both test and control wells. Next, (7) 5 cycles of 4i were performed with the sample without antibody staining and image acquisition, (8) followed by another round of IF (8× Elut.). (9) Primary and secondary antibodies were eluted from the sample (9× Elute) and (10) the sample was incubated with secondary antibodies only (SecAb only). Steps 7 to 10 were repeated twice (15× Elut., 21× Elut.).

Computation of Single-Cell Pixel Correlations

Pixel correlations were calculated between two 4i signals. If the signals were not recorded during the same acquisition, image alignment was performed prior to the correlation measurement. First, the same background value was subtracted from both images. Next, single pixel intensities of the two different 4i signals originating from the same cell were correlated in the segmented areas (Cell, Cytoplasm, Nucleus). This was done for every cell individually. Pixel correlations were calculated either with unsmoothed images or on images smoothed by either a 2×2, 3×3,5×5, 7×7, or 10×10 pixel mean filter. Pixel correlations in FIG. 1E and FIG. 3E were calculated as following. Pixel intensities of the first CTNNB1 staining (cycle 1) were correlated with each other CTNNB1 stain (odd cycles) up to the 21$^{st}$ cycle. Pixel intensities of the first TUBA1A staining (cycle 2) were correlated with each other TUBA1A stain (even cycles) up to the 20$^{th}$ cycle (green boxplots). Pixel intensity correlations between CTNNB1 and TUBA1A were calculated between the first CTNNB1 stain (cycle 1) and each TUBA1A staining (cycle 2, 4, 6, 8, 10, 12, 14, 16, 18, 20).

The calculated correlations over all cycles for each stain were aggregated in one box plot each and calculated after the corresponding images were smoothed by a mean filter of increasing size (none, 2×2, 3×3, 5×5, 7×7, and 10×10 pixel) pixels correlations of all cycles.

Image Alignment of Acquisition from Different 4i Cycles

Microscopy images of different cycles from the same site require image alignment, as slight shifts in X and Y occur in between acquisitions due to imperfect stage repositioning. Image registration based on Fast Fourier Transform was performed on DAPI images of two cycles. 488 nm and 568 nm acquisition, and segmentations masks were shifted by the calculated offset, resulting in aligned microscopy sites.

Example 1

Figure 3:
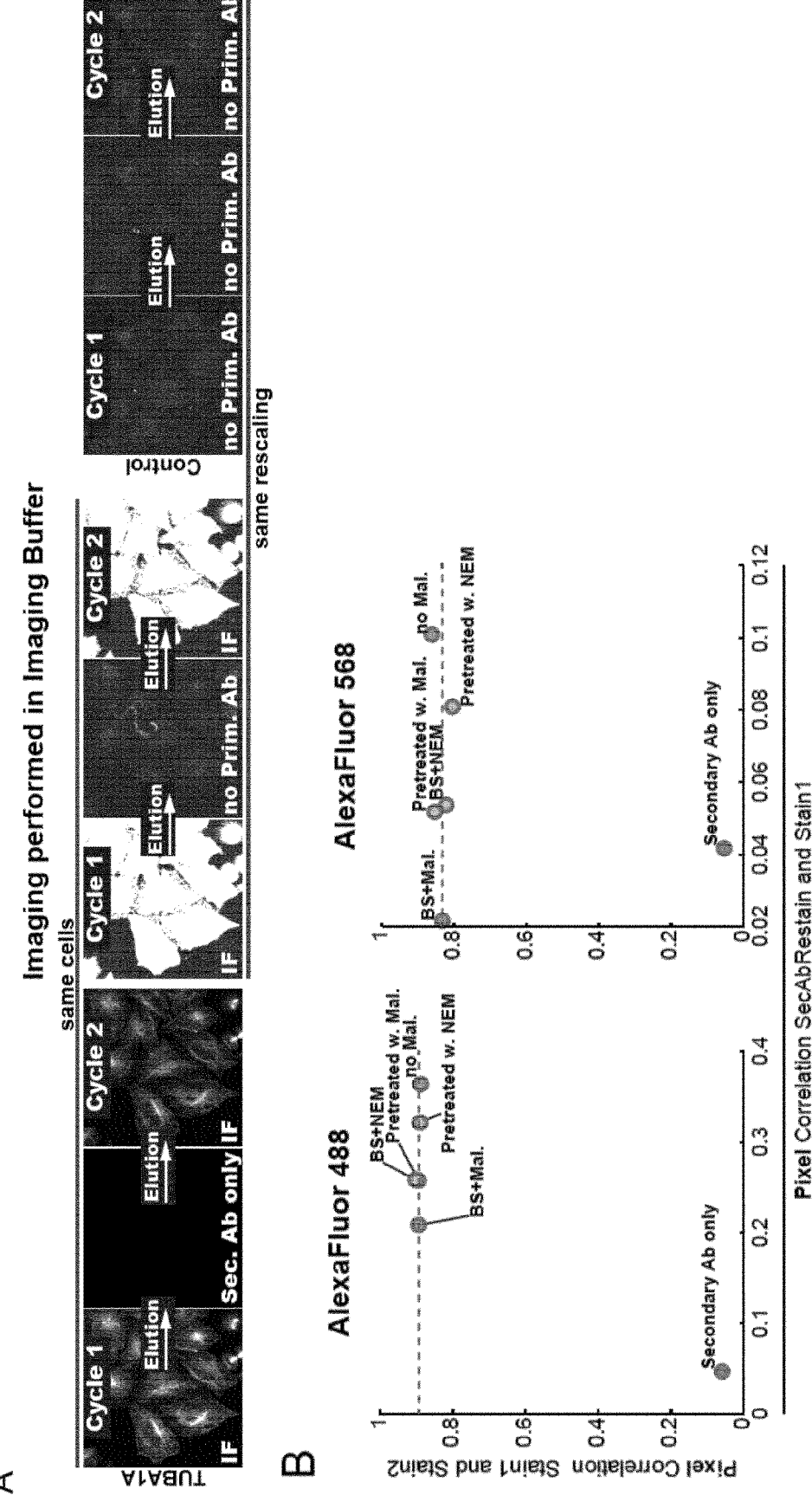
Figure 3:
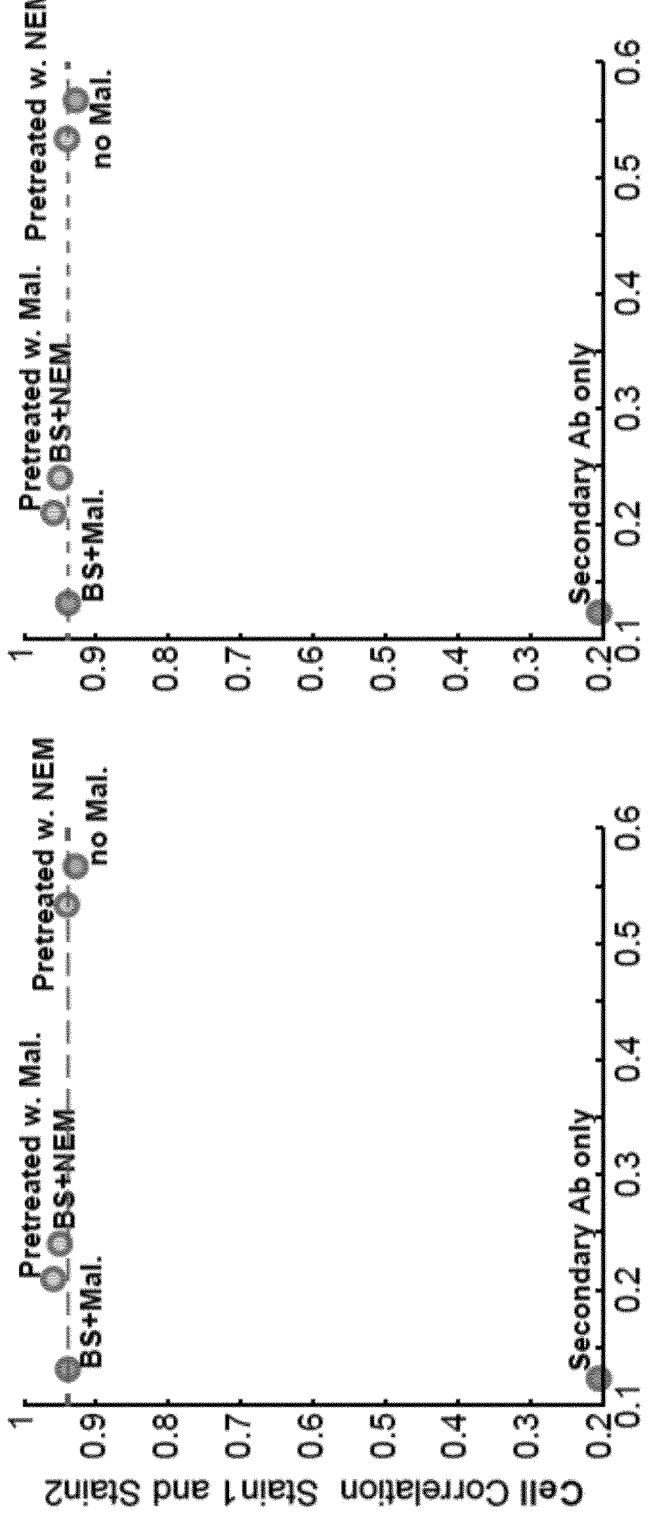
Figure 3:
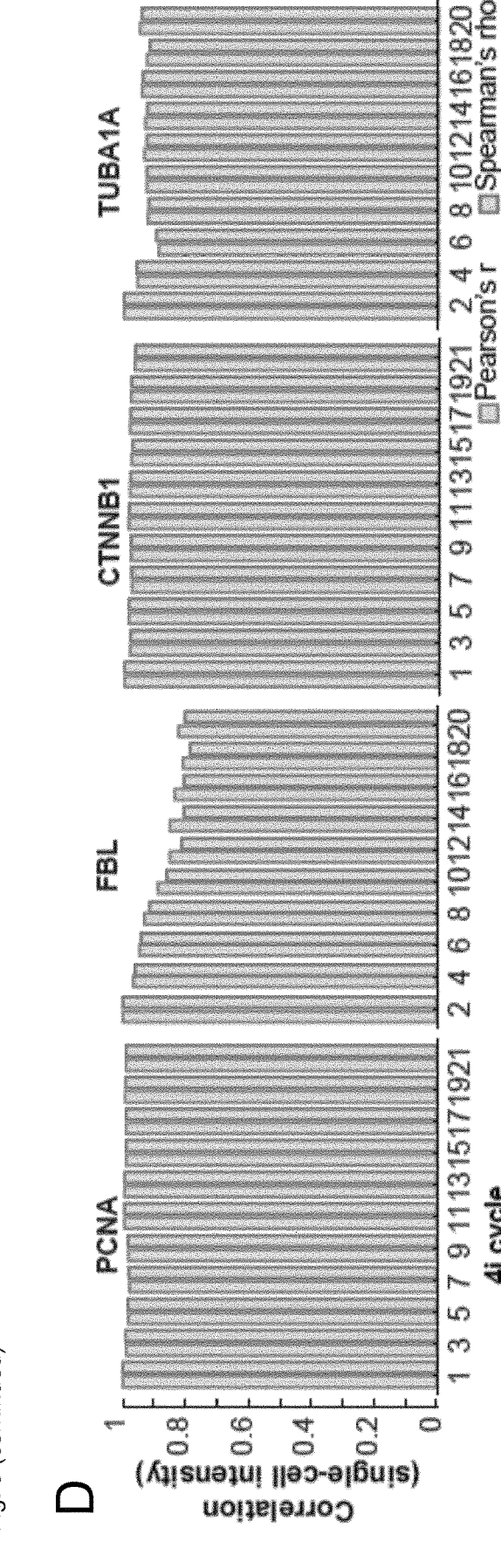
Figure 3:
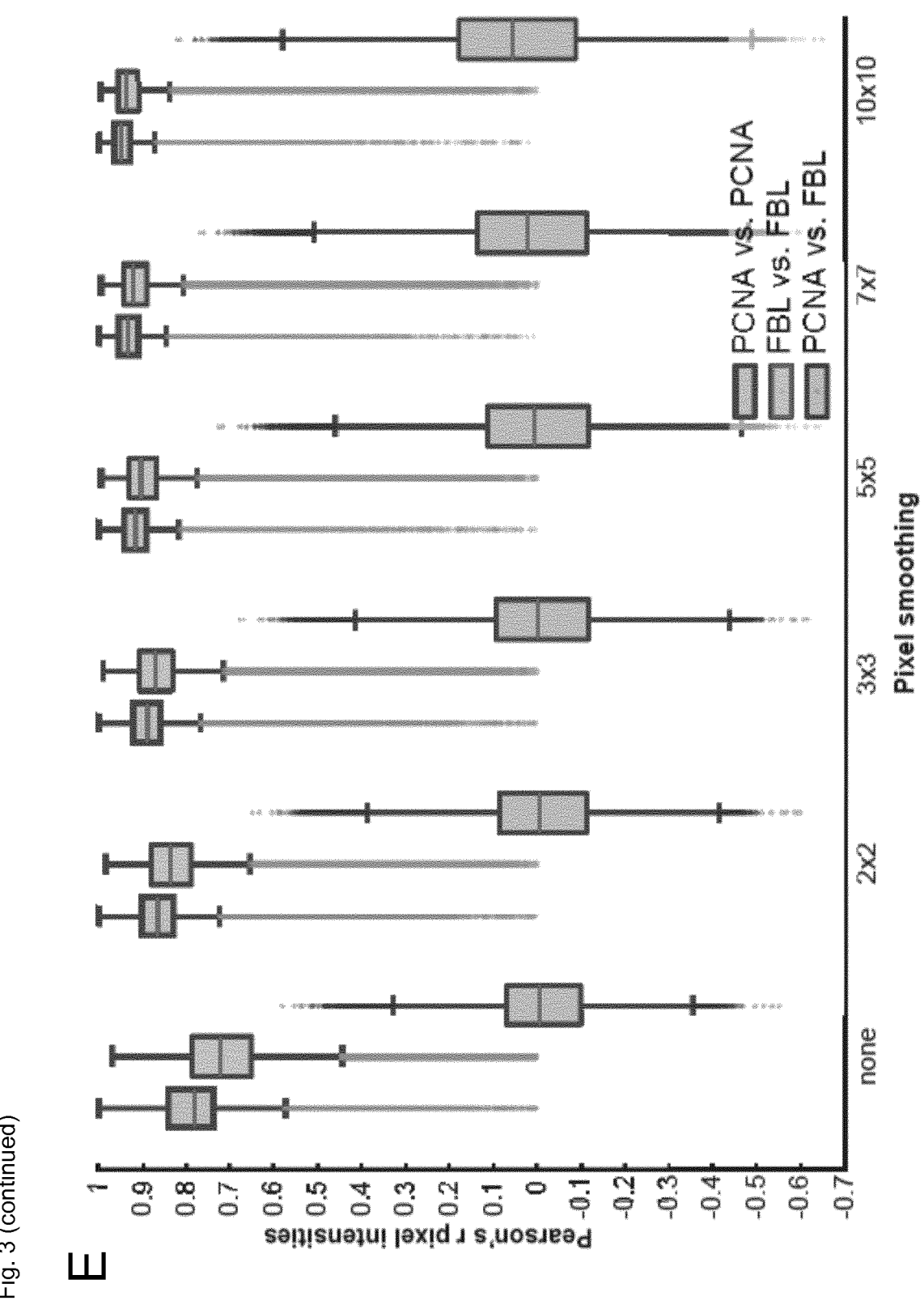

To obtain an approach that meets all requirements, the high-throughput multivariate imaging and computer vision approach (Snijder et al., (2009) Nature 461, 520-523; Liberali et al., (2014) Cell 157, 1473-1487; Battich et al., (2015). Cell 163, 1596-1610) was combined with an automated liquid handling platform that applies multiple iterations of staining, signal removal, and re-staining, a principle used in other fluorescence-based multiplexing approaches (Schubert et al., (2006). Nat Biotechnol 24, 1270-1278; Wahlby et al., (2002). Cytometry 47, 32-41; Lin et al., (2015). Nat Commun 6, 8390). Since photo-bleaching for signal removal was at these scales not practical, chemical antibody elution was chosen. Moreover, to be unrestricted in the choice of antibodies and not require primary antibody conjugations, the inventors turned to conventional indirect immunofluorescence, and made an unexpected discovery (FIG. 1A and FIG. 3A). When one site of the sample was imaged with an automated high-resolution spinning-disk confocal microscope after a standard immunofluorescence protocol (first imaging), the bound antibodies were eluted from the sample, re-stained with only secondary antibody, and the efficiency of antibody elution was checked (second imaging), the inventors observed that the elution efficiency was strongly compromised in the region that was exposed to light, but not in regions that were not exposed to light during the first round of imaging (FIG. 1A). This may be caused by the formation of singlet oxygen radicals during the excitation of fluorophores, which can introduce covalent bonds between reactive amino acids (methionine and cysteine) of proteins near the fluorophore, resulting in the crosslinking of antibodies to the sample during exposure to high-energy laser light used in confocal microscopy. Since this has gone unnoticed in previous antibody elution approaches, it may have prevented complete elution and led to the use of particularly harsh conditions that degrade the sample.

Next, it was screened through combinations of reagents that prevent such photo-induced crosslinking during imaging without reducing the efficiency of photon emission, and therefore allow complete antibody elution under very mild conditions that do not remove or degrade the antigen (FIG. 3B). This identified an imaging buffer that contains a low amount of a radical scavenger as well as an acceptor for free radical-induced photo-crosslinking, a very mild elution buffer, which relies on a reducing agent, low pH and chaotropic salt, and a blocking buffer that blocks free sulfhydryl groups in the sample. For more than 40 different antibodies, this combination achieved complete elution of primary and secondary antibodies over up to 21 iterations of staining and elution, the maximum number of cycles tested, whilst preventing any detectable loss or morphological changes in staining (FIG. 1B and FIG. 3B, C). Overlaying images obtained with the same antibodies in a 1st, 11th, and 21st round of staining resulted in almost perfect grey-scale images for various types of intracellular structures (FIG.

1C), and in very high single-cell and single-pixel intensity correlations between all rounds (FIG. 1D-E and FIG. 3D-E). Thus, the high-throughput automated iterative indirect immunofluorescence imaging approach (which is referred to as 4i) can obtain signals from surface areas as large as several mm² that are quantitatively reproducible over at least 20 iterations from subsamples as small as 165 by 165 nm, which corresponds to the surface area of a single pixel using a 40× objective and sCMOS camera.

Example 2

Figure 2:
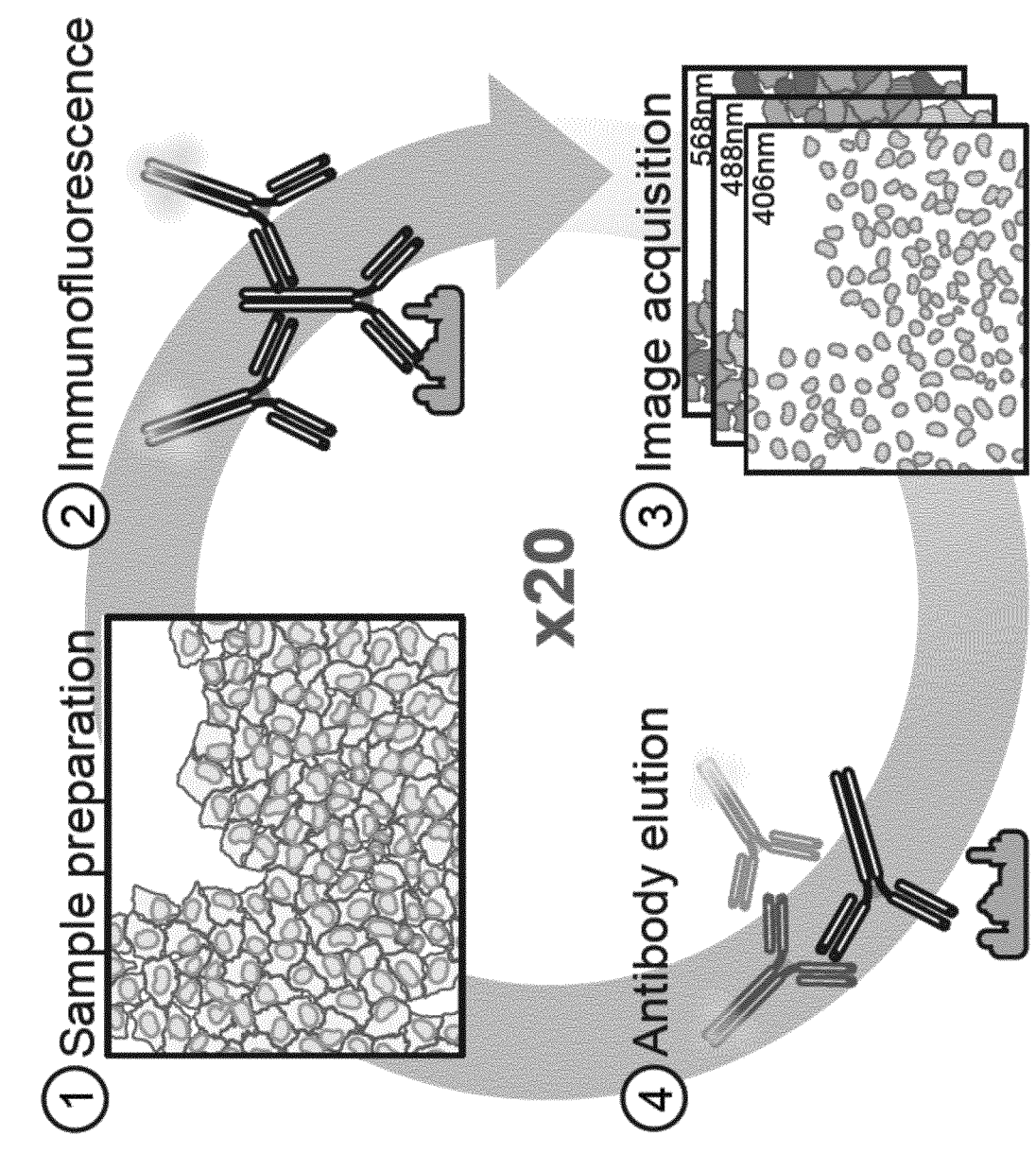
FIG. 2 Application of 4i in a high-throughput set up generates information across biological scales. Schematic representation of the 4i protocol. (1) The sample is blocked to prevent unspecific antibody binding and blocking of free sulfohydryls/thiols by thioether reaction with maleimide. (2) Indirect immunofluorescence (IF) against two different antigens of interest is performed. (3) Imaging Buffer is added to the sample and imaged. (4) Elution Buffer is used to elute primary and secondary antibodies from the sample, which is now ready to undergo another round of 4i.

Then, 4i was applied on human tissue culture cells (FIG. 2), covering the full cell height in 18 z-planes, and a total surface area of 9 mm², capturing ~20,000 single cells, for 11 different experimental conditions. Collectively, these images contain multivariate molecular and phenotypic information across several orders of magnitude of spatial scales, providing the possibility to directly study connections between multiple levels of biological organization. For instance, they allow visualizing the influence of local cell crowding on the abundance of an organelle, an emergent property at the cell population level, or of how position in the cell cycle influences the phosphorylated state of a protein, a property at the cellular level. At the same time, it allows assessing protein sub-compartmentalization, a property at the subcellular level, with enough resolution to capture the detailed morphology of cytoskeletal structures and organelles, such as microtubules, actin ruffles and focal adhesions, multiple types of endosomes, individual tubules of mitochondria, and ribbons of the Golgi complex, all in the same single cell and across hundreds of thousands of cells.

Discussion

The inventors have acquired 40 protein measurements that span the mm to the nm length scale in the same biological sample at high-throughput and for multiple conditions, and combined the information extracted from these various biological scales into one dataset. While existing protein multiplexing approaches have achieved similar levels of multiplexing for different subranges of these scales, none has spanned all simultaneously, either in low- or high-throughput. Moreover, the inventors achieve for the first time near comprehensive visualization of all intracellular organelles in the same cell. The underlying methodology is simple. 4i technology builds on a well-established high-throughput multivariate imaging platform combined with automated liquid handling that applies the proven principle of iterative staining and signal removal. 4i uses off-the-shelf antibodies without the need for special conjugations resulting in high signal yield due to the use of bright fluorophores and signal amplification by a secondary antibody. A crucial factor hereby is the prevention of photo-crosslinking during imaging, which enabled complete removal of both primary and secondary antibodies with a mild elution buffer, whilst fully preserving the sample even at the smallest spatial scale across a large number of cycles. This comes with the added advantage that epitope masking upon the detection of multiple antigens in close proximity is precluded. Excitingly, while the inventors have here restricted their analysis to 2D projections of single cells, their approach could also be applied to voxels for 3D analyses. In addition, their ability to obtain quantitatively reproducible single-pixel measurements promises 4i to be applicable in superresolution microscopy. In fact, highly multiplexed measurements on neighboring pixels may provide additional information that could increase the resolution of the image, as previously suggested. The ability to bridge biological length scales is one of the major challenges in the life sciences. Usually, extrapolation or inference is applied. However, in order to predict how properties at a higher scale emerge from multiple interactions occurring at a lower scale and how that feeds back on each other, it is necessary to cover multiple length scales within one measured dataset. Such datasets contain a richness of connections between scales that our current models of biological processes do not yet take into account. However, it is exactly through these connections by which gene expression is adapted to the cellular state, how a cell type is determined, how a pathological cellular phenotype emerges, or how a tumor cell responds to a drug.

The invention claimed is:

1. A method for multiplex staining of a biological sample, comprising the steps of:
   a. in a blocking step, contacting a biological sample prepared for imaging with a blocking solution, thereby producing a blocked biological sample, the blocking solution comprising
      i. a blocking compound that is capable of binding to hydrophobic binding sites non-specifically and
      ii. a sulfhydryl-reactive compound;
   b. in a first washing step, contacting said blocked biological sample with a washing solution; thereby producing a first washed biological sample;
   c. in a first staining step, contacting said first washed biological sample with a first antibody specific for a first antigen, thereby producing a first stained sample, wherein
      i. said first antibody bears a fluorescent label, or
      ii. said first antibody does not bear a fluorescent label, and subsequent to the first staining step, the first stained sample is contacted with the washing solution and a second staining step is performed, thereby producing a second stained sample, wherein said first stained sample is contacted with a second antibody that
         a. bears a fluorescent label, and
         b. is specific for the first antibody;
   d. in a second washing step, contacting said first stained sample or said second stained sample with the washing solution, thereby producing a second washed sample;
   e. in an imaging step, contacting said second washed sample with an imaging solution at neutral pH containing a radical scavenger, thereby producing an imaged sample and subsequently recording a fluorescence image of the second washed sample, thereby producing an imaged sample wherein the radical scavenger of the imaging solution is also an acceptor for free radical-induced photo-crosslinking;
   f. in a third washing step, contacting said imaged sample with the washing solution, thereby producing a third washed sample;
   g. in an elution step, contacting said third washed sample with an elution solution thereby producing an eluted sample, wherein the elution solution
      i. is characterized by a pH of about 2.2 to 4.0 and
      ii. comprises a buffering component, a reducing agent and at least one compound disrupting hydrogen bonds;
      wherein steps a to g are repeated 1 or more times, employing a different first antibody in each repeat.

2. The method according to claim 1, wherein directly before the imaging step (step (e)), the following steps are performed i. a nucleus-labelling step, contacting said second washed sample with a DNA-binding fluorescent compound, thereby producing a nucleus labelled sample;

ii. a washing step, contacting said nucleus labelled sample with the washing solution.

3. The method according to claim 1, wherein the blocking compound in the blocking solution is a blocking polypeptide and the compound in the elution solution disrupting hydrogen bonds is a chaotropic salt.

4. The method according to claim 1, wherein the blocking polypeptide is selected from the group consisting of bovine serum albumin (BSA), fetal bovine serum (FBS), serum albumin (SA), human serum, gelatin, skim milk powder and a polypeptide fraction of highly purified dermal collagen of porcine origin (PRIONEX® Reagent)

the sulfhydryl-reactive compound is selected from the group consisting of maleimide, haloacetyl, and pyridyl disulfide the radical scavenger is selected from the group consisting of N-acetylcysteine, N-acetylcysteine amide, cysteine, L-ascorbic acid, resveratrol, β-carotene, seleno-L-methionine, chlorogenic acid and caffeic acid the buffering component is selected from the group consisting of phosphate/citrate, potassium hydrogen phthalate and L-glycine the reducing agent is selected from the group consisting of tris(2-carboxyethyl)phosphine (TCEP), dithiothreitol, and 2-mercaptoethanol the chaotropic salt is selected from the group consisting of one or more of guanidinium chloride, urea, sodium dodecyl sulfate and magnesium chloride.

5. The method according to claim 1, wherein the blocking solution comprises 0.1 to 4% of the blocking compound selected from the group consisting of bovine serum albumin (BSA), fetal bovine serum (FBS), serum albumin (SA), human serum, gelatin, skim milk powder or PRIONEX® Reagent and/or 1 mmol/L to 1 mol/L of maleimide, haloacetyl, and pyridyl disulfide the imaging solution comprises 1 mmol/L to 1 mol/L of the radical scavenger selected from the group consisting of N-acetylcysteine, N-acetylcysteine amide, cysteine, L-ascorbic acid, resveratrol, β-carotene, seleno-L-methionine, chlorogenic acid and caffeic acid, and a pH of 7.2-7.6 the elution solution comprises 0.5 M L-glycine and 1 mmol/L to 1 mol/L of the compound disrupting hydrogen bonds selected from the group consisting of tris(2-carboxyethyl)phosphine (TCEP), dithiothreitol, and 2-mercaptoethanol and 1 mmol/L to 10 mol/L of one or more of guanidinium chloride, urea, sodium dodecyl sulfate and magnesium chloride, and a pH of 2.2-2.6.

6. The method according to claim 1, wherein the blocking solution comprises 1% bovine serum albumin (BSA) and 150 mM maleimide in phosphate buffered saline (PBS) and the imaging solution comprises 700 mM N-acetylcysteine in $H_2O$, at pH 7.4 the elution solution comprises 0.5 M L-glycine, 70 mM tris(2-carboxyethyl)phosphine (TCEP), 3 M guanidinium chloride and 3 M urea in $H_2O$ at pH 2.5.

7. The method according to claim 1, wherein the first antibody is incubated from 10 minutes to 16 hours the second antibody is incubated from 10 min to two hours the blocking solution is incubated from 5 min to one hour the elution solution is incubated for 1 minute to 30 minutes and all steps are performed at room temperature.

8. The method of claim 1, wherein the radical scavenger of the imaging solution is selected from the group consisting of N-acetylcysteine, N-acetylcysteine amide, and cysteine.

9. A kit comprising a blocking buffer, comprising:

a blocking compound that is capable of binding to hydrophobic binding sites non-specifically, wherein the blocking compound is a blocking polypeptide selected from the group consisting of bovine serum albumin (BSA), fetal bovine serum (FBS), serum albumin (SA), normal serum, gelatin, skim milk powder and PRIONEX® Reagent, an imaging buffer comprising a compound that is a radical scavenger selected from the group consisting of N-acetylcysteine, N-acetyl-cysteine amide, cysteine, L-ascorbic acid, resveratrol, β-carotene, seleno-L-methionine, chlorogenic acid and/or caffeic acid, and a pH of 7.2-7.6;

an elution buffer comprising a reducing agent that is selected from the group consisting of tris(2-carboxyethyl)phosphine (TCEP), dithiothreitol, or 2-mercaptoethanol and at least one compound disrupting hydrogen bonds selected from the group consisting of guanidinium chloride, urea, sodium dodecyl sulfate and magnesium chloride and L-glycine, and a pH of about 2.2 to 4.0.

10. The kit of parts according to claim 9, additionally comprising instructions to conduct a method for multiplex staining of a biological sample.

* * * * *